United States Patent [19]

Pirkle, Jr.

[11] Patent Number: 4,655,796

[45] Date of Patent: Apr. 7, 1987

[54] CONTINUOUS SORPTION PROCESS

[75] Inventor: James C. Pirkle, Jr., Lebanon, N.J.

[73] Assignee: Exxon Research & Engineering Co., Florham Park, N.J.

[21] Appl. No.: 537,850

[22] Filed: Sep. 30, 1983

[51] Int. Cl.[4] .............................................. B01D 53/12
[52] U.S. Cl. ............................................ 55/3; 55/75; 55/77; 210/661; 585/820
[58] Field of Search .................. 55/3, 75, 77, 99, 100; 210/222, 223; 585/820-822, 826-829

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,201,491 | 8/1965 | Stine et al. | 260/676 |
| 3,268,604 | 8/1966 | Boyd | 260/666 |
| 3,268,605 | 8/1966 | Boyd | 260/666 |
| 4,031,151 | 6/1977 | Healy et al. | 260/666 |
| 4,115,927 | 9/1978 | Rosensweig | 34/1 |
| 4,247,987 | 2/1981 | Coulalgiou et al. | 34/1 |
| 4,254,558 | 3/1981 | Mayer | 55/3 X |
| 4,283,204 | 8/1981 | Savage | 55/3 |
| 4,306,107 | 12/1981 | Broughton | 585/828 |
| 4,313,015 | 1/1982 | Broughton | 585/828 |
| 4,319,892 | 3/1982 | Waghorne et al. | 55/75 X |
| 4,319,893 | 3/1982 | Hatch et al. | 55/75 X |
| 4,436,533 | 3/1984 | Bannon | 55/75 X |
| 4,443,231 | 4/1984 | Siegell | 55/3 |

OTHER PUBLICATIONS

Bulk Separations Via Adsorption by D. B. Broughton, CEP. Oct. 1977, pp. 49-53.
An Energy-Saving Separation Scheme by R. W. Neuzil et al, Chemtech, Aug. 1980, pp. 498-502.

Primary Examiner—Robert Spitzer
Attorney, Agent, or Firm—M. D. Bittman; D. E. Furman

[57] ABSTRACT

The sorption process involves combining a simulated countercurrent flow system with a stationary magnetically stabilized fluidized bed to achieve continuous adsorption-desorption to separate components of a feed-stream.

10 Claims, 1 Drawing Figure

FIGURE I
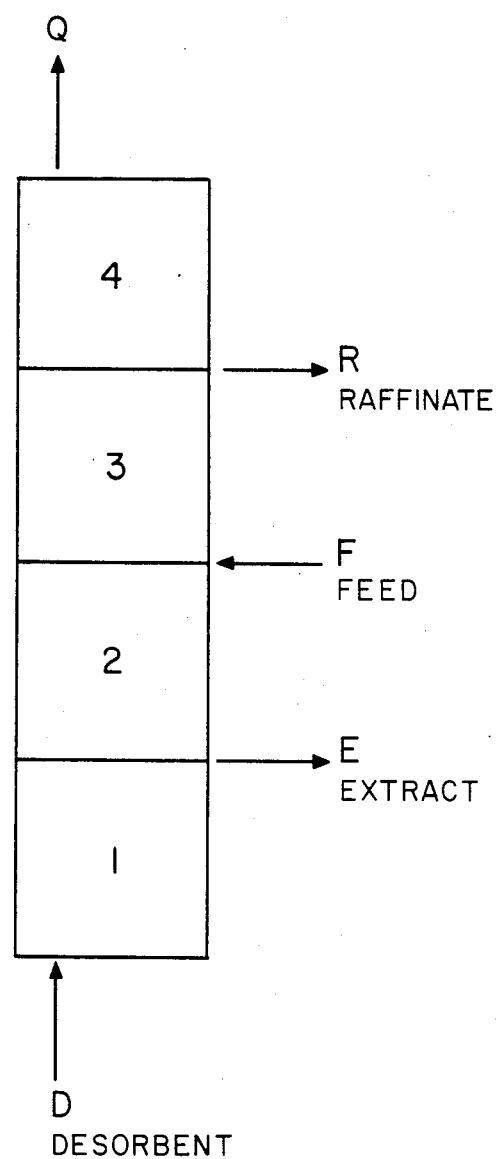

CONTINUOUS SORPTION PROCESS

BACKGROUND OF THE INVENTION

The present invention relates to a sorption process for the separation of components present within a mixture by contacting the mixture with a bed of magnetizable adsorbent particles wherein the adsorbent particles are magnetically stabilized in a stationary fluidized bed and in addition, contacting the adsorbent particles under conditions of simulated counter-current flow. More specifically, this separation process fluidizes the bed of magnetizable adsorbent particles while maintaining the bed in a stationary position and applies a magnetic field to the bed of adsorbent particles at a strength sufficient to suppress solids backmixing and fluid by-passing, and to preserve staging. A continuous process is provided by contacting the feedstream with the adsorbent in a simulated countercurrent flow system wherein the stream flows upwards trough a desorption zone, one or more rectification zones and an adsorption zone, each zone being serially and circularly interconnected and divided into a plurality of serially interconnected sections, each section containing adsorbent with the points of introduction and withdrawal of the streams into and from the sections being simultaneously and periodically shifted to simulate countercurrent flow.

The present sorption process by combining simulated countercurrent flow with a magnetically stabilized fluidized bed process has advantages over either of these processes taken alone. Among the advantages are that axial dispersion in a static (stationary) magnetically stabilized bed appears to be lower than that of a moving magnetically stabilized bed. In addition, since there will be less movement of particles in a static magnetically stabilized bed, there will be less attrition of the particles and therefore less need to replace the particles. Also, since the particles are stationary the uniform dispersion of the particles within the zones will be easier to maintain than in a moving bed configuration, with the uniform dispersion of particles bearing directly on the efficiency of separation achieved. Further, there will be no need to provide transportation systems for removing and introducing the particles continuously into the magnetically stabilized bed as in a moving bed system, thereby saving the capital and energy expenditures associated therewith.

In fixed bed adsorption process, the process is limited by particle size of the adsorbent material due to the high resistance to passage of the fluid through a fixed bed of small particles, while there is no such resistance to fluid throughput for small particles in a fluidized magnetically stabilized bed. Further, since small particles can be used in the present sorption process, separations become more distinct and resultant recoveries and purities are improved. The high resistance to fluid flow through fixed beds of smaller particles will require higher pressure drops across the bed to ensure adequate fluid throughput, thus subjecting the bed to excessive mechanical stress and contributing to attrition of solid particles. Reducing fluid flow through a fixed bed of smaller particles to provide a lower pressure drop across the bed would not be economical, since a low throughput of feed corresponds to a process that is less economical. Another advantage of a fluidized magnetically stabilized bed over a fixed bed is the lack of gravitational stresses on the particles which helps reduce attrition of solids. In addition, the magnetically stabilized bed allows poisoned or otherwise deactivated sorbent to be rapidly replaced with far less shutdown time than is required for fixed beds, since fixed beds generally require careful reloading to avoid channeling of fluid through the bed.

The prior art discloses a number of simulated countercurrent flow systems wherein a continuous process is used in connection with fixed beds by simultaneously and periodically shifting points of introduction and withdrawal of the streams in order to simulate the countercurrent flow of the adsorbent particles and the feed. U.S. Pat. Nos. 2,985,589, 3,040,777, and 3,201,491 disclose the use of such simultaneous and periodic shifting of the feed and withdrawal points, specifically through use of a rotary valve. U.S. Pat. Nos. 3,268,605, 3,268,604 and 4,031,151 also disclose simulated countercurrent flow systems.

Various processes for operating magnetically stabilized fluidized beds for uses such as separations are disclosd in the art, including U.S. Pat. Nos. 4,155,927, 4,247,987, and 4,283,204. However, common to the separation processes disclosed in these patents are that the bed of particles move (e.g. in a plug-flow manner) against the contacting fluid stream creating a countercurrent flow of fluid and particles. This countercurrent flow requires the particles to be removed from the vessel and reintroduced. The present sorption process does not move the particles of the magnetically stabilized fluidized bed, but maintains the particles in a stationary position and utilizes a simulated countercurrent flow system to provide a continuous separation process which maintains the advantages of a continuous process and the advantages of a magnetically stabilized fluidized bed.

SUMMARY OF THE INVENTION

Briefly, the present invention provides a continuous process for separating the components of a feedstream wherein at least one component is selectively adsorbed by contact with a bed of magnetizable adsorbent particles comprising continuously contacting the feedstream with the adsorbent utilizing a simulated countercurrent flow system. In this flow system the feed stream flows upward through a desorption zone, rectification zone and adsorption zone each zone being serially and circularly interconnected and divided into a plurality of sections each section containing adsorbent. The point of introduction and withdrawal of the streams into and from the sections are simultaneously and periodically shifted to simulate the countercurrent flow. The adsorbent particles are fluidized by contacting the particles with a fluid flowing in an ascending manner against the force of gravity. The bed of adsorbent particles are maintained in a stationary position and a magnetic field is applied to the bed at a strength sufficent to suppress any solids backmixing and fluid bypassing, and to preserve staging. The adsorbed components of the feedstream are desorbed with a stream of desorbent introduced into the bed with separated streams of adsorbed and relatively lesser adsorbed components being withdrawn from the bed.

BRIEF DESCRIPTION OF THE DRAWING

FIG. I is a flow scheme showing the continuous sorption process of this invention.

DETAILED DESCRIPTION OF THE INVENTION

The separation process of this invention involves combining the simulated countercurrent flow system with a magnetically stabilized fluidized bed to achieve continuous adsorption-desorption to separate components of a feedstream. In carrying out the process, the feedstream is continously contacted with the adsorbent utilizing a simulated countercurrent flow system wherein the fluid streams flow upward through a desorption zone, rectification zone and an adsorption zone, each zone being serially and circularly interconnected and divided into a plurality of interconnected sections each section containing adsorbent. The simulated countercurrent flow of adsorbent particles and feedstream is achieved by simultaneously and periodically shifting the points of introductions and withdrawal of the streams into and from the sections. In this way the introduction of feedstream and the withdrawal of separated streams of adsorbed and relatively less adsorbed components is achieved in a continuous manner. Any suitable apparatus comprising a series of beds or one, single continuous bed of adsorbent, if desired, having fluid-flow connecting means between the outlet of one bed and the inlet of the next adjacent bed and comprising a suitable means, such as a valve or manifold, for shifting the points of inlet and outlet for the various feed and product streams involved in the process may be provided. Suitable valve arrangements for shifting points of introduction and withdrawal are disclosed in U.S. Pat. Nos. 2,985,589, 3,040,777, 3,201,491 and 3,268,604 which disclose switching valves (rotary valves) and control systems for simulated moving bed processes.

Optionally, in addition to the usual extract and raffinate streams, an intermediate raffinate stream can be taken off the column at about the midpoint of the adsorption zone in order to separate a second and third component from the feedstream. The intermediate raffinate stream is withdrawn at a locus approximately midway between the upstream and downstream boundaries of said adsorption zone, i.e. midpoint between the point of introduction of the feed stream and point of withdrawal of the raffinate stream. This intermediate raffinate stream is simultaneously and periodically shifted to simulate countercurrent flow along with the extract and raffinate streams. The withdrawal of such an intermediate raffinate stream is described in U.S. Pat. Nos. 4,306,107 and 4,313,015 which are incorporated herein by reference.

Concurrently with using the simulated countercurrent flow system, a magnetically stabilized fluidized bed is employed. The magnetically stabilized fluidized bed enables the process to be operated at a higher fluid throughput and when smaller particles are utilized increased efficiencies of separation can be achieved. The bed of adsorbent particles is fluidized by contacting the particles with a fluid flowing in an ascending manner against the force of gravity. Unlike common simulated countercurrent flow systems, fluid flow in the configuration of the present invention will be upwards through the bed instead of downward. This is necessary to keep the bed of adsorbent particles fluidized and slightly expanded, with a magnetic field being applied to stabilize the bed. A magnetic field is applied to the bed of adsorbent particles at a strength sufficient to suppress solids backmixing and fluid bypassing and to preserve staging of the particles within the bed, with the bed of adsorbent particles being maintained in a stationary position. The components which are adsorbed onto the adsorbent particles are desorbed with a stream of desorbent which is introduced into the bed of adsorbent particles and separated streams of adsorbed and relatively lesser adsorbed components are withdrawn from the bed.

More specifically, the simulated countercurrent flow is described as an adsorption separation column which is divided into three (or four) equivalent zones (see FIG. I): an adsorption zone 3, a (primary) rectification zone 2, a desorption zone 1 and (a secondary rectification zone 4). An upstream portion (relative to fluid flow) of the adsorption zone is also called a primary rectification zone. These zones are serially interconnected in order and a continuously circulated fluid stream flowing through the three (or four) zones is maintained by circulating the effluent fluid from an outlet of the last zone to an inlet of the first zone; all the points of introducing and withdrawing the inlet and outlet streams are simultaneously shifted, at stated intervals of time, in a downstream direction relative to the fluid flow (or upwards on the bed) to provide thereby a simulated countercurrent flow system wherein there is achieved a processing effect similar to that observed with the solids moving in the moving-bed type adsorption process. Since the fluid flow is upwards through the bed, the inlet and outlet streams must be also shifted upwards to simulate a downflow of sorbent.

This process for a simulated countercurrent flow system in an adsorption-separation process may be described as follows. In such a process, at least one of the components of the feed mixture is selectively sorbed by contact with solid adsorbent particles; said feed mixture is allowed to flow through these serially and circularly interconnected zones, a desorption zone, a rectification zone and an adsorption zone, each zone being divided into a plurality of serially interconnected sections, each section containing adsorbent particles; introducing a desorbent stream into the first section of the desorption zone; introducing the feed mixture to the first section of the adsorption zone and withdrawing a raffinate effluent comprising a less sorbed component and the desorbent from the adsorption zone; withrawing an extract effluent comprising the sorbed component and desorbent from the desorption zone; from a secondary rectification zone a relatively pure stream of desorbent flows to the interconnected desorption zone; and all the points of introducing and withdrawing the streams into and from the sections are simultaneously shifted, at stated intervals of time, in a downstream direction relative to the fluid flow, while maintaining the same order of continuity and the same spatial relationship between all the points. While separate beds may be utilized for each of the zones a single continuous bed may be utilized with each of the zones being defined by points of inlet and points of withdrawal of the various streams flowing into and out of the bed. Between the zones, as well as having input and withdrawal points, there can be introduced mixing zones to promote uniformity of dispersion of the fluid streams flowing through the zones.

The magnetizable adsorbent particles in the adsorption separation column are fluidized by contacting the bed of particles with a fluid in an ascending manner against the force of gravity. This flow of fluid opposing the external force field of gravity is at a superficial fluid velocity ranging between the lower limit provided by the minimum fluidization superficial fluid velocity required to fluidize the bed in the absence of a magnetic field and an upper limit given by the superficial fluid velocity required to destabilize the bed, that is, cause solid backmixing, channeling or other turbulence within the bed. The superficial fluid velocity of the fluidizing fluid in case of a gas, may range from about 0.005 to about 3 m/sec., preferably 0.01 to 1 and in case of a liquid, would range from 0.005 cm/sec. to about 10 cm/sec. and preferably from 0.1 to 1 cm/sec. The strength of the magnetic field applied to the bed of adsorbent magnetizable particles critically is such as to suppress solid backmixing and prevent fluid bypassing and preserve staging of the particles (e.g. prevents channeling of fluid through the bed). Typically, the magnetic field would range from about 50 to about 1500 Oersted, preferably from about 60 to 600 Oersted. The process of this invention can be carried out in the gas and/or liquid phase, that is, with the fluid, feed and desorbent being in the gas or liquid state.

The fluidizing fluid is introduced in a continuous manner through the bed of adsorbent particles to maintain the bed in the fluidized mode. The fluidizing fluid will preferably contain the desorbent which is continuously circulated through the bed of adsorbent particles. The desorbent is generally a material capable of displacing adsorbed components of the feedstream already adsorbed on the adsorbent particles. The fluidizing fluid and desorbent may also contain an inert material which is a liquid or gas which is not significantly adsorbed by the adsorbent in the presence of the feedstream.

The fluid stream flowing through the zones thus comprises a mixture of desorbent and desorbed sorbate released from an upstream bed of adsorbent (relative to fluid flow), It is preferred that the boiling point of the desorbent and inert material differ sufficiently (e.g. by 15° C.) from the feedstream components to be readily separable therefrom by suitable means, such as simple distillation. Suitable desorbents useful in a $C_8$ aromatic isomer separation process include toluene, m-diisopropylbenzene (m-DIPB), p-diethylbenzene (p-DEB), mixtures of diethylbenzene isomers (DEB), o-dichlorobenzene (o-DEB) and the like. Suitable inert desorbent diluents include but are not limited to paraffinic materials having from 8 to 16 carbon atoms. The extract (containing the more adsorbed components) and raffinate (containing the less adsorbed components) streams withdrawn from the column may be fractionated to separate the desorbent from the relatively pure adsorbed of the extract or from the less strongly adsorbedd feed component in the raffinate.

The sorption process is applicable to a process for separating a component from a feedstream containing a mixture of components. In a preferred process the separations are made among components which are relatively difficult to separate from one another by means such as fractionation, such as close boiling isomers. One particularly useful application of this process is in the separation of aromatic isomers, such as $C_8$, $C_9$ and $C_{10}$'s. For example, the sorption process may be used for the separation of the $C_8$ aromatic isomers of ethylbenzene, paraxylene, orthoxylene and metaxylene from one another utilizing particular crystalline metal-aluminosilicate adsorbent materials.

The adsorbent used in this invention is any solid particle capable of selectively adsorbing a desired component from the feedstream. The preferred adsorbent particles include crystalline metal-aluminosilicate adsorbents, which are especially useful in the separation of the aromatic isomers, including the xylene isomers. Examples of such useful metal-aluminosilicate adsorbents are the Zeolites X or Y which have been substituted with metallic ions such as potassium, barium, etc. or combinations thereof. The choice of adsorbent and substitution of metallic ions is well within the skill of the art.

The adsorbent particle used in this invention must additionally be magnetizable. The adsorbent particle may be a composite of an adsorbent material, a magnetizable material, that is, a material which is magnetic in an externally applied magnetic field or which is magnetic per se and, if needed, a binder. The magnetizable material can be a ferromagnetic substance such as iron, nickel, cobalt, etc. For example, a 50 micron or smaller stainless steel powder is useful. The composite can be prepared by admixing the magnetic particles and the adsorbent (for example a zeolite sieve) with a base for the adsorbent forming a relatively homogeneous gel. The adsorbent base may be comprised, for example, of silica, alumina, or alumina-silica. The gel is then dried, calcined and sized. Suitable techniques for sizing and shaping the composite adsorbent are extrusion, pilling, beading, spray drying etc. The magnetizable component may also be composited with the adsorbent by impregnation, cogelling, coprecipitation, etc.

The adsorbent particles will typically have an average diameter ranging from 50–1500 microns preferably 100 to 1000 microns. The particles may be any shape; for example, spherical, irregular shaped or elongated.

In applying the present invention to a commercial sorption-desorption system for separating $C_8$ aromatic isomers, the operating temperatures may vary from case to case. In general, however, the operable temperatures are generally in the range of from about 60° to 300° C. for the gas phase with pressures from atmospheric to 10 atm., while the liquid phase temperatures are generally in the range of 0° to 200° C. with pressures of from 1 to 30 atmospheres.

EXAMPLE 1

An example of a separation is the liquid phase recovery of paraxylene from a mixture of $C_8$ aromatic hydrocarbons. The feedstream contains a mixture of 25% paraxylene, 25% ethylbenzene, 25% metaxylene, and 25% orthoxylene by weight.

A four zone separation scheme as shown in FIG. I is used. With the adsorbent having more affinity for paraxylene than the other $C_8$ species, the purpose of zone 3 (adsorption zone) is to keep paraxylene out of stream R (raffinate). The purpose of zone 2 (primary rectification zone) is to keep the weaker adsorbing $C_8$ species out of the nearly pure paraxylene stream E (extract). Zone I (desorpton zone) is used to desorb paraxylene from sorbent at the bottom of the column. Zone 4 (secondary rectification zone) is used to clean up some of the desorbent by adsorbing the lighter $C_8$'s out of stream Q. Alternatively, without zone 4 the desorbent can be cleaned up by means such as fractionation. The remainder of the desorbent D is recovered by downstream separation (e.g. fractionation) from streams R and E. These zones are serially inteconnected in order and a continuous stream of fluid is circulated through the zones. All points of introducing and withdrawing the inlet and outlet streams are periodically and simultaneously shifted in a downstream direction (relative to liquid flow) to provide a simulated countercurrent flow system.

The following is the adsorbent and fluid flow conditions for the separation of paraxylene in the liquid phase utilizing KY Zeolite.

The adsorbent particles are a composite of 35% KY zeolite, 15% clay binder and 50% stainless steel powder (by weight) with a particle size of 0.02 cm and a density of 1.9 gm/cc. The shifting of inlet and outlet streams is carried out at a rate to simulate the downstream motion of adsorbent at a velocity of about 0.575 cm/sec. The volume of adsorbent is approximately 2.7 cubic meters, which occupies approximately half the volume of the column. The selectivities of the KY zeolite for paraxylene/metaxylene is 6.0, for para-xylene/ethylbenzene is 1.7, for paraxylene/orthoxylene 4.5 and paraxylene/toluene is 1.4. The desorbent is pure toluene. The fluidizing fluid (toluene) passes through the column at an initial superficial fluid velocity of 0.147 cm/sec. The column diameter is 0.757 meters with a column height of about 12 meters divided approximately evenly among the four zones. The separation column is surrounded by electromagnets to provide a magnetic field in the bed. A magnetic field of 60 to 600 oersted is applied at a level effective to stabilize the fluidized adsorbent particles, the bed of particles being maintained in a stationary position. The flow rates for the various streams is as follows: feed (F)=39.7 Kg-Moles/Day; desorbent (fluidizing fluid) (D)=536 Kg-Moles/Day; raffinate (R)=209 Kg-Moles/Day; extract (E)=186 Kg Moles/Day; and desorbent recovery (Q)=180 Kg-Moles/Day.

The composition of the extract, raffinate and desorbent streams (shown in FIG. I) are as follows:
Stream R (Raffinate)
    4.7 Mole % Ethyl benzene
    4.7 Mole % Meta-xylene
    85.9 Mole % Toluene
    0.01 Mole % Para-xylene
    4.7 Mole % Ortho-xylene
Stream E (Extract)
    0.025 Mole % Ethyl benzene
    <0.001 Mole % Meta-xylene
    94.64 Mole % Toluene
    5.33 Mole % Para-xylene
    <0.001 Mole % Ortho-xylene
Stream Q (Desorbent Recovery)
    <0.1 Mole % Ethyl benzene
    <0.1 Mole % Meta-xylene
    >99.6 Mole % Toluene
    <0.1 Mole % Para-xylene
    <0.1 Mole % Ortho-xylene Thus, the sorption process effectively produces an extract stream which contains paraxylene with the other $C_8$ isomers excluded and a raffinate stream which contains the other lesser adsorbed $C_8$ isomers with paraxylene excluded.

What is claimed is:

1. A continuous process for separating the components of a feedstream wherein at least one component is selectively adsorbed by contact with a bed of magnetizable adsorbent particles comprising:
    continuously contacting the feedstream with the bed of adsorbent particles utilizing a simulated countercurrent flow system wherein the streams flow upward through a desorption zone, a rectification zone, and an adsorption zone, each zone being serially and circularly interconnected and divided into a plurality of interconnected sections, each section containing the bed of adsorbent particles, with the points of introduction and withdrawal of the streams into and from the sections being simultaneously and periodically shifted to simulate countercurrent flow;
    fludizing the bed of adsorbent particles by contacting the adsorbent with a fluid flowing in an ascending manner against the force of gravity, the bed of adsorbent particles being maintained in a stationary position;
    applying a magnetic field to the bed of adsorbent particles at a strength sufficient to suppress solids backmixing and fluid bypassing and to preserve staging; and
    desorbing the adsorbed components with a stream of desorbent introduced into the bed of adsorbent particles and withdrawing separated streams of more adsorbed and relatively lesser adsorbed components.

2. Process of claim 1 further comprising a secondary rectification zone.

3. Process of claim 2 wherein the fluidizing fluid contains the desorbent which is continuously circulating through the bed of adsorbent particles.

4. Process of claim 3 wherein the feedstream and fluid are liquid.

5. Process of claim 4 wherein the magnetizable adsorbent particles are a composite containing a magnetizable material and a crystalline metal aluminosilicate.

6. Process of claim 5 wherein the adsorbent particles have an average diameter of 50 to 1500 microns.

7. Process of claim 6 wherein the feedstream comprises $C_8$ to $C_{10}$ aromatics.

8. Process of claim 6 wherein the magnetic field ranges from 60 to 600 Oersted and the fluidizing fluid flows at a velocity of 0.005 to 10 cm/sec.

9. Process of claim 3 further comprising withdrawing an intermediate raffinate stream at a locus approximately midway between the upstream and downstream boundaries of said adsorption zone.

10. Process of claim 3 wherein the zones are all contained within one column containing a single continuous bed of adsorbent particles.

* * * * *